US012790370B2

(12) United States Patent
Durocher et al.

(10) Patent No.: US 12,790,370 B2
(45) Date of Patent: Nov. 10, 2026

(54) VIRAL ORIGIN OF REPLICATION TO INCREASE PROTEIN PRODUCTIVITY FROM MAMMALIAN CELLS

(71) Applicant: National Research Council of Canada, Ottawa (CA)

(72) Inventors: Yves Durocher, Montreal (CA); Sylvie Perret, Montreal (CA); Simon Joubert, Laval (CA)

(73) Assignee: National Research Council of Canada, Ottawa (CA)

( * ) Notice: Subject to any disclaimer, the term of this patent is extended or adjusted under 35 U.S.C. 154(b) by 1228 days.

(21) Appl. No.: 17/767,219

(22) PCT Filed: Oct. 27, 2020

(86) PCT No.: PCT/IB2020/060060
§ 371 (c)(1),
(2) Date: Apr. 7, 2022

(87) PCT Pub. No.: WO2021/084418
PCT Pub. Date: May 6, 2021

(65) Prior Publication Data

US 2022/0363723 A1 Nov. 17, 2022

Related U.S. Application Data

(60) Provisional application No. 62/927,833, filed on Oct. 30, 2019.

(51) Int. Cl.
*C07K 14/05* (2006.01)
*C07K 16/28* (2006.01)

(52) U.S. Cl.
CPC .......... *C07K 14/05* (2013.01); *C07K 16/2863* (2013.01)

(58) Field of Classification Search
CPC ............................ C07K 14/05; C07K 16/2863
See application file for complete search history.

(56) References Cited

U.S. PATENT DOCUMENTS

| | | | | |
|---|---|---|---|---|
| 8,637,315 | B2 | 1/2014 | Durocher et al. | |
| 9,085,627 | B2 | 7/2015 | Durocher et al. | |
| 2014/0051170 | A1* | 2/2014 | Durocher | C12N 15/85 |

FOREIGN PATENT DOCUMENTS

| | | | | |
|---|---|---|---|---|
| WO | 2009137911 | A1 | 11/2009 | |
| WO | WO2017032834 | A1 * | 3/2017 | C12N 15/85 |

OTHER PUBLICATIONS

Stuible et al., "Optimization of a high-cell-density polyethylenimine transfection method for rapid protein production in CHO-EBNA1 cells". Journal of Biotechnology, pp. 39-47. (Year: 2018).*
Yates et al., "The Minimal Replicator of Epstein-Barr Virus oriP", Journal of Virology, pp. 4512-4522 (Year: 2000).*
(Continued)

*Primary Examiner* — Sharmila G Landau
(74) *Attorney, Agent, or Firm* — Jessica Smith

(57) ABSTRACT

The present disclosure relates to the use of an Epstein Barr virus origin of replication (oriP) or a functional fragment thereof in a protein expression construct to increase production of a protein of interest in mammalian cells. Also disclosed are protein expression constructs for increased production of antibodies in mammalian cells, and mammalian cells containing the expression constructs.

12 Claims, 10 Drawing Sheets

Specification includes a Sequence Listing.

(56) References Cited

OTHER PUBLICATIONS

Craenenbroeck et al., "Episomal vectors for gene expression in mammalian cells", European Journal of Biochemistry, pp. 5665-5678 (Year: 2001).*
McKenzie & Abbott, "Expression of recombinant proteins in insect and mammalian cells", Methods, pp. 40-49 (Year: 2018).*
Frappier, "The Epstein-Barr Virus EBNA1 Protein", Scientifica, pp. 1-15 (Year: 2012).*
Shirakata & Hirai, "Identification of Minimal oriP of Epstein-Barr Virus Required for DNA Replication", J. Biochem, pp. 175-181. (Year: 1997).*
Harrison et al., "Sequence Requirements of the Epstein-Barr Virus Latent Origin of DNA Replication", Journal of Virology, p. 1913-1925 (Year: 1994).*
Kishida et al., "Pleiotrophic functions of Epstein-Barr virus nuclear antigen-1 (EBNA-1) and oriP differentially contribute to the efficacy of transfection/expression of exogenous gene in mammalian cells", Journal of Biotechnology, pp. 201-207 (Year: 2008).*
Tomiyasu, Ki-ichiro, et al. "Gene Transferin vitroandin vivowith Epstein-Barr Virus-Based Episomal Vector Results in Markedly High Transient Expression in Rodent Cells." Biochemical and biophysical research communications 253.3 (1998): 733-738.
Reisman, David, and Bill Sugden. "trans activation of an Epstein-Barr viral transcriptional enhancer by the Epstein-Barr viral nuclear antigen 1." Molecular and cellular biology 6.11 (1986): 3838-3846.
Extended European Search Report for EP application No. 20883092.7, dated Mar. 4, 2024.
Mullick et al., The cumate gene-switch: a system for regulated expression in mammalian cells. BMC Biotechnology, 2006, 6:43.
Durocher et al., High-level and high-throughput recombinant protein production by transient transfection of suspension-growing human 293-EBNA1 cells, Nucleic Acids Research, 2002, 30(2): 1-9.
Poulain et al., Rapid protein production from stable CHO cell pools using plasmid vector and the cumate gene-switch. Journal of Biotechnology, 2017, 255:16-27.
Nanbo et al., The coupling of synthesis and partitioning of EBV's plasmid replicon is revealed in live cells. EMBO Journal, 2007, 26(19): 4252-4262.
Yates et al., Stable replication of plasmids derived from Epstein-Barr virus in various mammalian cells, Nature, 1985, 313: 812-815.
Tanaka et al., Construction of epstein-barr virus-based expression vector containing mini-OriP, Biochemical and Biophysical Research Communications, 2000, 264: 938-943.
Yates et al., The minimal replicator of Epstein-Barr virus oriP, Journal of Virology, 2000, 74(10): 4512-4522.
ISR-WO for PCT/IB2020/060060 dated Jan. 15, 2021.
Kennedy, G. and B. Sugden, EBNA-1, a bifunctional transcriptional activator. Molecular and Cellular Biology, 2003, 23(19): 6901-6908.
Poulain et al., Reducing recombinant protein expression during CHO pool selection enhances frequency of high-producing cells. Journal of Biotechnology, 2019, 296: 32-41.
Van Craenenbroeck et al, Episomal vectors for gene expression in mammalian cells, Eur. J. Biochem. 267, 5665-5678, 2000.

* cited by examiner

Fig. 6

```
mini oriP      1 -----------------------------------------------------------------accct
OriP        1751 gtagctaccgataagcggaccctcaagagggcattagcaatagtgtttataaggcccccttgtta.....

mini oriP      6 aaacgggtagcatatgcttcccgggtagtagtatatactatccagactaaccctaattcaatagcatatg
OriP        1681 ......................................................................

mini oriP     76 ttacccaacgggaagcatatgctatcgaattagggttagtaaaagggtcctaaggaacagcgat------
OriP        1611 ................................................................atctcc

mini oriP        ----------------------------------------------------------------------
OriP        1541 caccccatgagctgtcacggttttatttacatggggtcaggattccacgagggtagtgaaccattttagt

mini oriP        ----------------------------------------------------------------------
OriP        1471 cacaagggcagtggctgaagatcaaggagcgggcagtgaactctcctgaatcttcgcctgcttcttcatt

mini oriP        ----------------------------------------------------------------------
OriP        1401 ctccttcgtttagctaatagaataactgctgagttgtgaacagtaaggtgtatgtgaggtgctcgaaaac

mini oriP        ----------------------------------------------------------------------
OriP        1331 aaggtttcaggtgacgcccccagaataaaatttggacgggggggttcagtggtggcattgtgctatgacac

mini oriP        ----------------------------------------------------------------------
OriP        1261 caatataaccctcacaaaccccttgggcaataaatactagtgtaggaatgaaacattctgaatatcttta

mini oriP        ----------------------------------------------------------------------
OriP        1191 acaatagaaatccatggggtggggacaagccgtaaagactggatgtccatctcacacgaatttatggcta

mini oriP        ----------------------------------------------------------------------
OriP        1121 tgggcaacacataatcctagtgcaatatgatactggggttattaagatgtgtcccaggcagggaccaaga

mini oriP        ----------------------------------------------------------------------
OriP        1051 caggtgaaccatgttgttacactctatttgtaacaaggggaaagagagtggacgccgacagcagcggact

mini oriP        ----------------------------------------------------------------------
OriP         981 ccactggttgtctctaacacccccgaaaattaaacggggctccacgccaatggggcccataaacaaagac

mini oriP        ----------------------------------------------------------------------
OriP         911 aagtggccactcttttttttgaaattgtggagtgggggcacgcgtcagcccccacacgccgccctgcggt

mini oriP        ----------------------------------------------------------------------
OriP         841 tttggactgtaaaataagggtgtaataacttggctgattgtaaccccgctaaccactgcggtcaaaccac

mini oriP    140 ---------------------------------------------gtaggtgggcggccaagatagggg
OriP         771 ttgcccacaaaaccactaatggcaccccggggaatacctgcataa.........................

mini oriP    165 cgcgattgctgcgatctggaggacaaattacacacacttgcgcctgagcgccaagcacagggttgttggt
OriP         701 ......................................................................

mini oriP    235 cctcatattcacgaggtcgctgagagcacggtgggctaatgttgccatgggtagcatatactacccaaat
OriP         631 ......................................................................

mini oriP    305 atctggatagcatatgctatcctaatctatatctgggtagcataggctatcctaatctatatctgggtag
OriP         561 ......................................................................

mini oriP    375 catatgctatcctaatctatatctgggtagtatatgctatcctaatttatatctgggtagcataggctat
OriP         491 ......................................................................

mini oriP    445 cctaatctatatctgggtagcatatgctatcctaatctatatctgggtagtatatgctatcctaatctgt
OriP         421 ......................................................................

mini oriP    515 atccgggtagcatatgctatcctaatagagattagggtagtatatgctatcctaatttatatctgggtag
OriP         351 ......................................................................

mini oriP    585 catatactacccaaatatctggatagcatatgctatcctaatctatatctgggtagcatatgctatccta
OriP         281 ......................................................................

mini oriP    655 atctatatctgggtagcataggctatcctaatctatatctgggtagcatatgctatcctaatctatatct
OriP         211 ......................................................................

mini oriP    725 gggtagtatatgctatcctaatttatatctgggtagcataggctatcctaatctatatctgggtagcata
OriP         141 ......................................................................

mini oriP    795 tgctatcctaatctatatctgggtagtatatgctatcctaatctgtatccgggtagcatatgctatcctc
OriP          71 ......................................................................

mini oriP    865 a
OriP           1 .
```

VIRAL ORIGIN OF REPLICATION TO INCREASE PROTEIN PRODUCTIVITY FROM MAMMALIAN CELLS

CROSS-REFERENCE TO RELATED APPLICATIONS

This application is a national phase entry of International Patent Application No. PCT/IB2020/060060 filed Oct. 27, 2020, and claims the benefit of U.S. provisional application No. 62/927,833 filed Oct. 30, 2019, the entire contents of each of which is herein incorporated by reference in its entirety.

FIELD

The present disclosure relates to the use of a viral origin of replication (oriP) in a protein expression construct to increase production of a protein of interest in mammalian cells. Also disclosed are protein expression constructs for increased production of antibodies in mammalian cells, and mammalian cells containing the expression constructs.

INTRODUCTION

Human or animal cells are routinely used in academia and industry to produce proteins. Proteins can be produced through transient or stable protein expression. For stable protein expression, generally a stable pool of cells which can be used for production is first generated, and/or cells within this pool are cloned to identify cell lines that are good producers. Either way, scientists are looking to increase productivity of the cells to reduce cost of production.

Several ways are used to increase protein production from stably expressing cells such as modifying the codons of the gene of interest, modifying the promoter, incorporating Scaffold/Matrix Attachment Region (S/MAR) or Ubiquitous Chromatin Opening Element (UCOE) elements, improving the cell culture media and feeds, better selecting the high expressing cells. Other methods to increase protein production from stable pools or cell lines are needed.

SUMMARY

The present inventors have demonstrated that incorporation of the EBV oriP sequence in an expression plasmid is able to increase protein production in the selected CHO pools and clones, even in the absence of EBV's EBNA1 protein.

The EBNA1 protein EBV oriP system was used in the transient transfection of CHO-3E7 platform to increase protein production. The present inventors investigated the use of the EBNA1 protein EBV oriP system for increasing productivity in stable cell lines. The presence of oriP per se was found to increase productivity of stable pools, and presence of EBNA1 in the cell line did not increase the productivity in this context.

Accordingly, one aspect of the disclosure is a nucleic acid construct for the expression of a protein of interest. The nucleic acid construct of the disclosure comprises a) at least one expression cassette comprising a DNA sequence encoding a protein of interest operably linked to a promoter and a transcription termination site; b) a selectable marker; and c) an Epstein Barr Virus (EBV) origin of replication (oriP) or functional fragment thereof comprising a dyad symmetry (DS) region and a family of repeats (FR) segment. In an embodiment, the oriP or functional fragment thereof has at least 90% identity to the sequence of SEQ ID NO: 1 or SEQ ID NO: 2.

In an embodiment, the nucleic acid construct further comprises a Scaffold Attachment Region (SAR).

In an embodiment, the promoter is an inducible promoter, optionally a tetracycline response element (TRE), a ponA-inducible promoter, or a cumate-inducible promoter.

In an embodiment, the promoter is a constitutive promoter, optionally a human Ubiquitin C (UBC) promoter, human Elongation Factor 1 alpha (EF1A) promoter, human phosphoglycerate kinase 1 (PGK) promoter, simian virus 40 early promoter (SV40), cytomegalovirus immediate-early promoter (CMV) promoter, chicken b-Actin promoter coupled with CMV early enhancer (CAG), the hybrid EF1-HTLV promoter, or the Chinese hamster EF1 promoter (CHEF).

In an embodiment, the selectable marker is a neomycin resistance gene, a hygromycin resistance gene, a puromycin resistance gene, blasticidin resistance gene, zeocin resistance gene or optionally a Glutamine Synthetase (GS) gene.

In an embodiment, the expression cassette encodes an antibody or antibody fragment, or an antibody heavy chain and/or an antibody light chain.

In some embodiments, the nucleic acid construct comprises two expression cassettes. In an embodiment, one expression cassette encodes an antibody heavy chain and one expression cassette encodes an antibody light chain.

Another aspect of the disclosure is a method of production of a protein of interest, the method comprising: a) introducing into a mammalian cell the nucleic acid construct of the disclosure; b) applying selective pressure to the cell to select for cells that carry the selectable marker; and c) culturing the cell under conditions for production of the protein of interest. In some embodiments two different nucleic acid constructs of the disclosure are introduced into the mammalian cell.

In one embodiment, the nucleic acid construct or constructs are introduced into the cell by transfection. In some embodiments, the transfection is carried out by a transfection reagent such as a cationic lipid, a non-liposomal reagent, or a cationic polymer. Optionally the cationic polymer is polyethylenimine (PEI). In other embodiments, the transfection is calcium phosphate transfection or electroporation/nucleofection.

In one embodiment protein production is increased by at least 5%, at least 10%, at least 20%, at least 30%, at least 40%, at least 50%, at least 60%, at least 70%, at least 80%, at least 90%, at least 100%, at least 150%, at least 200%, or at least 250% relative to protein production in a cell from a nucleic acid construct lacking an oriP when cultured under the same conditions.

In one embodiment, the mammalian cell is a SP2/0 cell, NS/0 cell, HT-1080 cell, PER.C6 cell, HKB-11 cell, CAP cell, HUH-7 cell, Chinese Hamster Ovary (CHO) cell or a Human Embryonic Kidney 293 (HEK293) cell. In one embodiment, the cell does not express EBNA1.

In an embodiment, the selectable marker is glutamine synthetase (GS) and the selective pressure applied is the withdrawal of glutamine from a growth medium. In another embodiment, the selective agent is methionine sulfoximine (MSX) selection of glutamine synthetase overexpressing cells. In yet another embodiment, the selective marker is methotrexate selection of dihydrofolate reductase (DHFR) expressing cells.

In another embodiment, the promoter is an inducible promoter and the conditions for the production of the protein of interest comprise the addition of an inducing agent.

In a further embodiment, the nucleic acid is integrated into the genome of the mammalian cell.

In one embodiment, the method further comprises collecting the mammalian cell and/or a cell medium containing the protein of interest, and optionally purifying the protein of interest from the collected cell and/or the cell medium.

In some embodiments, the nucleic acid encodes an antibody fragment, an antibody heavy chain and/or an antibody light chain. In some embodiments, the protein of interest is an antibody or antibody fragment, optionally cetuximab or a fragment thereof.

A further aspect of the disclosure is a mammalian cell for increased production of a protein of interest comprising one or more nucleic acids constructs of the disclosure. In some embodiments, the cell comprises two different nucleic acid constructs of the disclosure, each encoding a different protein of interest. In some embodiments, the protein of interest is an antibody or an antibody fragment, optionally cetuximab or a fragment thereof.

In some embodiments, the nucleic acid construct or constructs are stably transfected, optionally the construct or constructs are integrated into the genome of the mammalian cell.

In some embodiments the mammalian cell is a Chinese Hamster Ovary (CHO) cell or a Human Embryonic Kidney 293 (HEK293) cell. In one embodiment, the cell does not express EBNA1.

The preceding section is provided by way of example only and is not intended to be limiting on the scope of the present disclosure and appended claims. Additional objects and advantages associated with the compositions and methods of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages, objects and embodiments are expressly included within the scope of the present disclosure. The publications and other materials used herein to illuminate the background of the disclosure, and in particular cases, to provide additional details respecting the practice, are incorporated by reference, and for convenience are listed in the appended reference section.

DRAWINGS

Further objects, features and advantages of the disclosure will become apparent from the following detailed description taken in conjunction with the accompanying figures showing illustrative embodiments of the disclosure, in which:

FIG. 6 shows a sequence alignment of truncated (mini) oriP (SEQ ID NO:1) vs full-length oriP (SEQ ID NO:2).

DESCRIPTION OF VARIOUS EMBODIMENTS

Figure 1A:
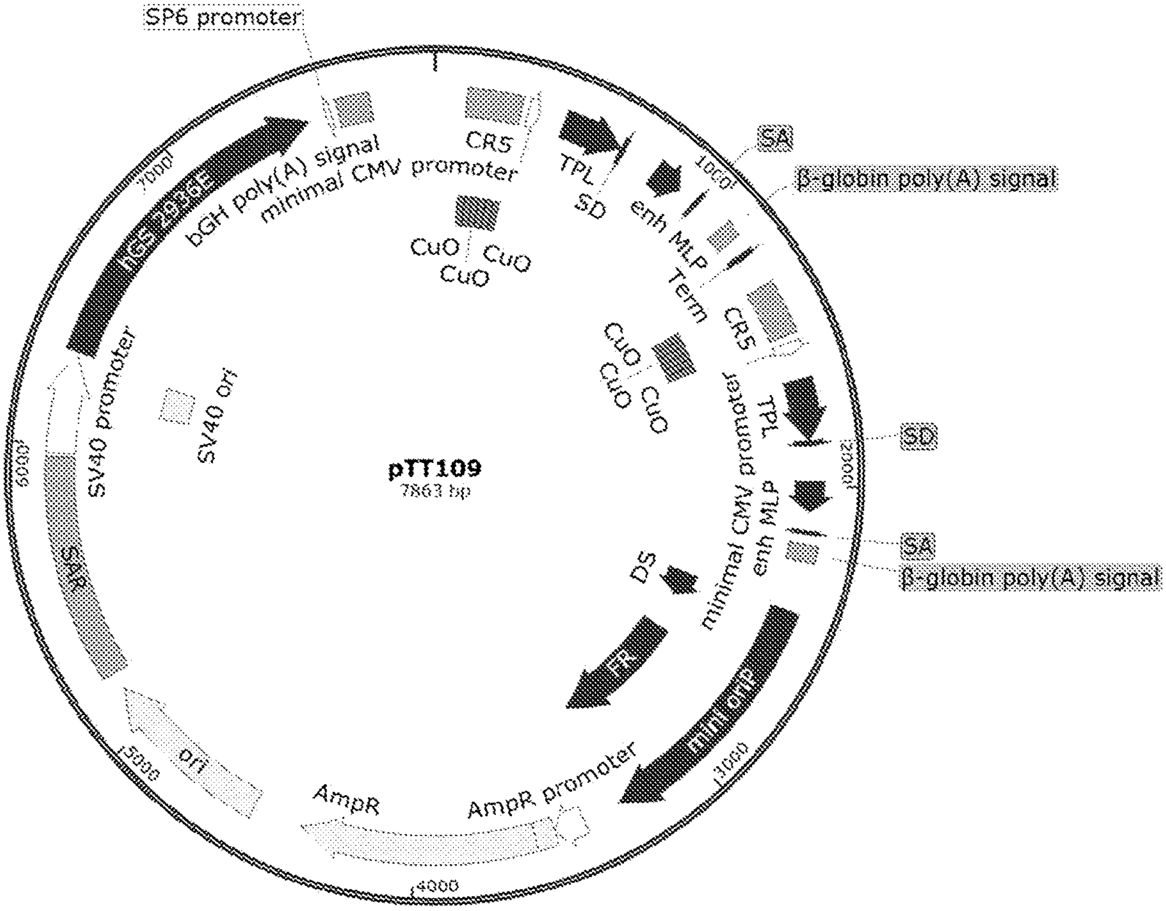
FIG. 1A shows pTT109™ plasmid map.
Figure 1B:
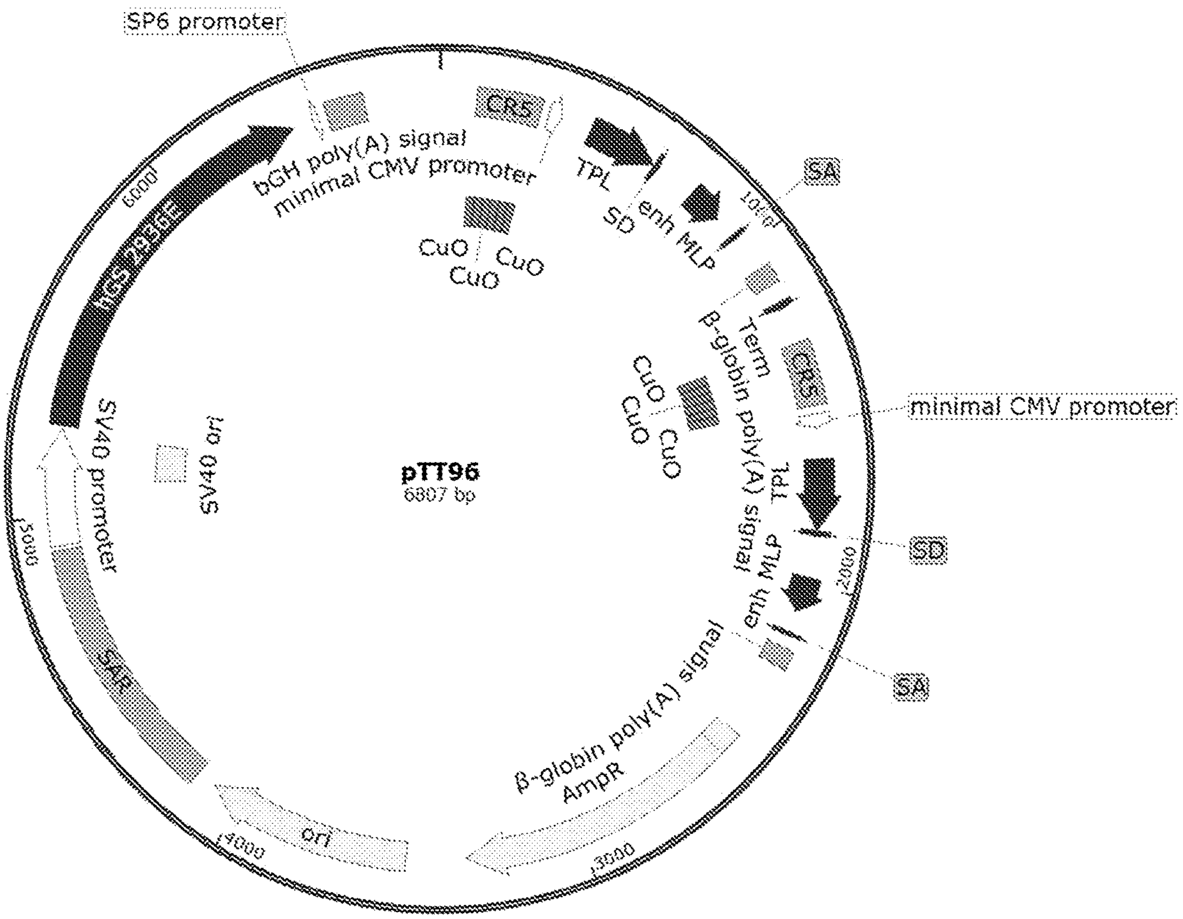
FIG. 1B shows pTT96™ plasmid map.
Figure 1C:
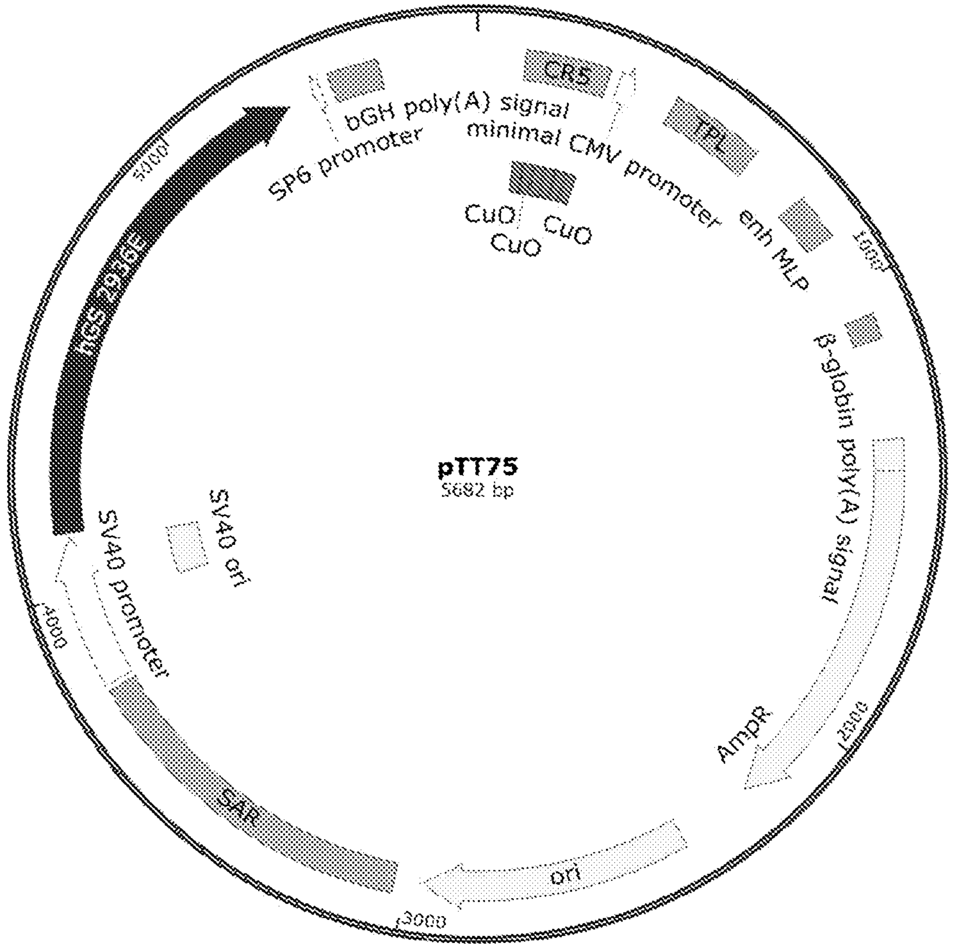
FIG. 1C shows pTT75™ plasmid map.
Figure 1D:
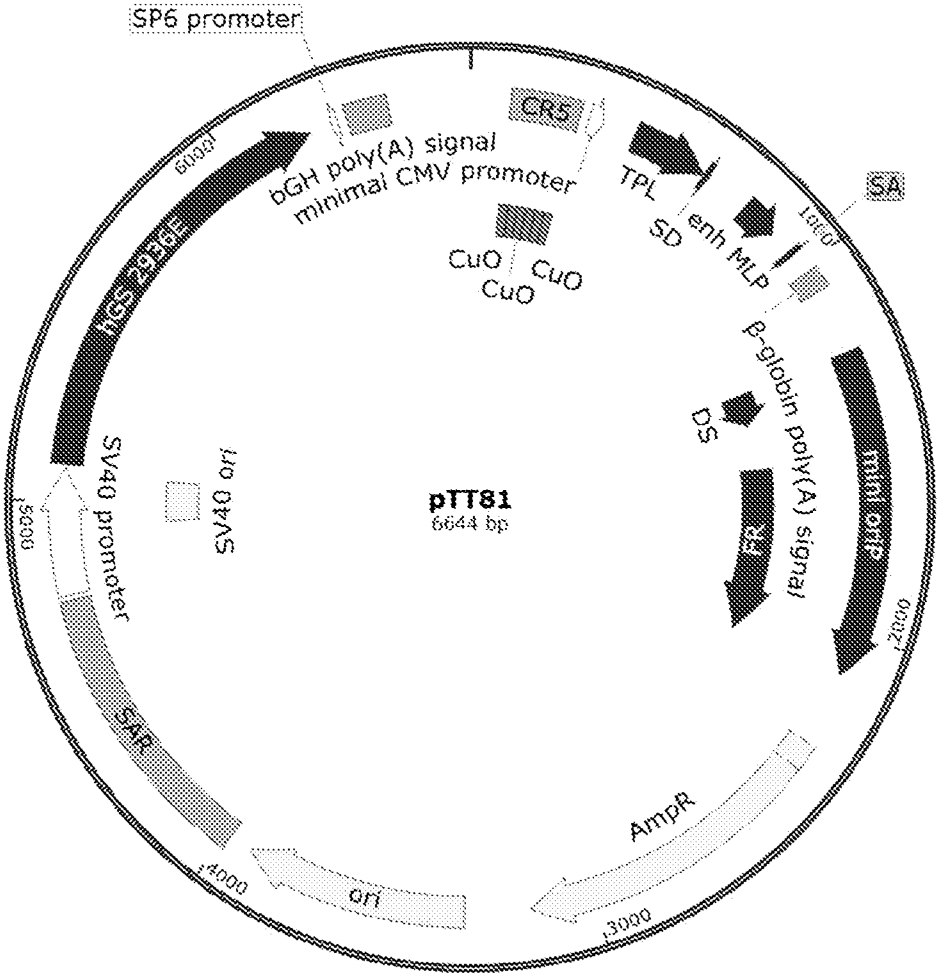
FIG. 1D shows pTT81™ plasmid map.

The following is a detailed description provided to aid those skilled in the art in practicing the present disclosure. Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

I. DEFINITIONS

As used herein, the following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present specification, including definitions, will control. In addition, the materials, methods, and examples are illustrative only and not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated. The upper and lower limits of these smaller ranges which may independently be included in the smaller ranges is also encompassed within the description, subject to any specifically excluded limit in the stated range. Where the stated range includes one or both of the limits, ranges excluding either both of those included limits are also included in the description.

It must be noted that as used herein and in the appended claims, the singular forms "a", "an", and "the" include plural references unless the context clearly dictates otherwise.

All numerical values within the detailed description and the claims herein are modified by "about" or "approximately" the indicated value, and take into account experimental error and variations that would be expected by a person having ordinary skill in the art.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The term "about" as used herein means plus or minus 10%-15%, 5-10%, or optionally about 5% of the number to which reference is being made.

It should also be understood that, in certain methods described herein that include more than one step or act, the order of the steps or acts of the method is not necessarily limited to the order in which the steps or acts of the method are recited unless the context indicates otherwise.

II. COMPOSITIONS OF MATTER

The incorporation of the EBV oriP sequence in an expression plasmid was found to increase production of proteins of interest in selected CHO pools and clones in the absence of EBV's EBNA1 protein. Accordingly, provided herein are nucleic acid constructs useful for increased expression of a protein of interest.

The term "nucleic acid construct of the disclosure" as used herein refers to a nucleic acid construct comprising a) at least one expression cassette comprising a DNA sequence encoding a protein of interest operably linked to a promoter and a transcription termination site; b) a selectable marker; and c) an EBV oriP or functional fragment thereof, comprising a dyad symmetry (DS) region and a family of repeats (FR) segment.

The term "nucleic acid molecule" and its derivatives, as used herein, are intended to include unmodified DNA or RNA or modified DNA or RNA. For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "operably linked" as used herein refers to a relationship between two components that allows them to function in an intended manner. For example, where a reporter gene is operably linked to a promoter, the promoter actuates expression of the reporter gene.

The term "promoter" or "promoter sequence" generally refers to a regulatory DNA sequence capable of being bound by an RNA polymerase to initiate transcription of a downstream (i.e. 3') sequence to generate an RNA. Suitable promoters may be derived from any organism and may be bound or recognized by any RNA polymerase. Suitable promoters for the expression cassette will be known to the skilled person. In some embodiments, the promoter is an inducible promoter. Examples of inducible promoters include, without limitation, a tetracycline response element (TRE) (e.g. Tet-ON or Tet-OFF systems), ponA-inducible expression systems (Agilent Technologies), or cumate-inducible promoters such as CuO (System Biosciences). In some embodiments, the promoter is a constitutive promoter. Examples of constitutive promoters include human Ubiquitin C (UBC) promoter, human Elongation Factor 1 alpha (EF1A) promoter, human phosphoglycerate kinase 1 (PGK) promoter, simian virus 40 early promoter (SV40) promoter (GenBank accession number J02400.1), cytomegalovirus immediate-early promoter (CMV), chicken b-Actin promoter coupled with CMV early enhancer (CAG), EF1-HTLV hybrid promoter, and Chinese hamster EF1 promoter (CHEF).

The term "transcription termination site" as used herein refers generally to a polyadenylation signal (pA) that terminates transcription of messenger RNA (mRNA). Suitable pAs may be derived from any organism and are known to the skilled person. Examples of pA signals include, without limitation, rabbit beta-globin pA (GenBank accession number K03256), SV40 late polyA, hGH polyA and strong bovine growth hormone pA (BGHpA) (GenBank accession number M57764.1).

The term "selectable marker" as used herein refers to an element in a nucleic acid construct that confers a selective advantage to cells harboring the nucleic acid construct. For example, the selectable marker may encode a protein that is expressed and confers resistance to a specific drug. Alternatively, the selectable marker may encode a protein that is expressed and is essential for cell viability under specific growth conditions. Suitable selectable markers are known to the skilled person. Examples of suitable drug-selectable markers include, without limitation, markers that confer neomycin resistance, hygromycin resistance, blasticidin resistance, zeocin resistance or puromycin resistance. Such markers are also referred to as resistance genes. Examples of genes required for growth under specific growth conditions include, without limitation, Glutamine Synthetase (GS) (GenBank accession number AY486122.1) and dihydrofolate reductase (DHFR).

The term "oriP" as used herein refers to the origin of viral replication found within the Epstein Barr virus episome comprising a dyad symmetry (DS) region and a family of repeats (FR) segment, or a functional fragment thereof. The Epstein Barr Virus (EBV) oriP has twenty-four EBNA1 binding sites, including four in the DS region, where replication is initiated, as well as a 20 sites in the FR segment. In an embodiment, the EBV oriP or functional fragment thereof comprises a sequence as shown in SEQ ID NO: 1 or SEQ ID NO: 2 or a functional variant thereof.

The term "functional variant" as used herein includes modifications of the nucleic acid sequences disclosed herein that perform substantially the same function as the nucleic acid molecules disclosed herein in substantially the same way.

In one embodiment, the present disclosure includes functional variants to the nucleic acid sequences of an oriP disclosed herein. The functional variants include nucleotide sequences that hybridize to the nucleic acid sequences set out above, under at least moderately stringent hybridization conditions, optionally under stringent hybridization conditions.

By "at least moderately stringent hybridization conditions" it is meant that conditions are selected which promote selective hybridization between two complementary nucleic acid molecules in solution. The term "at least moderately stringent hybridization conditions" encompasses stringent hybridization conditions and moderately stringent hybridization conditions. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log10 [Na+])+0.41(%(G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm-5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

In another embodiment, the functional variant nucleic acid sequences of the oriP comprise sequences having at least 50%, or at least 60%, or at least 70%, or at least 80%, or at least 90%, at least 95%, at least 99%, or 100% sequence identity to the oriP of SEQ ID NO: 1 and/or SEQ ID NO: 2 disclosed herein.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, the nucleic acid construct further comprises a Scaffold Attachment Region (SAR) or a Scaffold/Matrix Attachment Region (S/MAR), which are A/T rich sequences. The SAR may be derived from any organism and will be known to the skilled person. In some embodiments the SAR contains 750 nucleotides from the Human interferon alpha2 upstream scaffold associated region 3, nucleic acid sequence positions 1000 to 1751 (GenBank accession number U82705.1). In other embodiments, the nucleic acid construct further comprises a Ubiquitous Chromatin Opening Element (UCOE), which are G/C rich sequences.

The nucleic acid construct described herein may comprise two expression cassettes to allow for the expression of two proteins of interest from the same nucleic acid construct. The additional expression cassette may comprise the same or a different promoter and/or the same or a different pA signal.

In some embodiments, the nucleic acid construct encodes an antibody fragment, an antibody heavy chain and/or an antibody light chain. The antibody fragment, antibody heavy chain and/or antibody light chain may be encoded on separate nucleic acid constructs or may be encoded by two expression cassettes on the same nucleic acid construct.

The term "antibody" as used herein is intended to include monoclonal antibodies, polyclonal antibodies, chimeric and humanized antibodies. The term "antibody fragment" as used herein is intended to include without limitations Fab, Fab', F(ab')2, scFv, dsFv, ds-scFv, Fc-fusion proteins, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, Fc-fusion proteins, dimers, minibodies, diabodies, bispecific antibody fragments and other fragments can also be synthesized by recombinant techniques.

The basic antibody structural unit is known to comprise a tetramer composed of two identical pairs of polypeptide chains, each pair having one light ("L") (about 25 kDa) and one heavy ("H") chain (about 50-70 kDa). The amino-terminal portion of the light chain forms a light chain variable domain (VL) and the amino-terminal portion of the heavy chain forms a heavy chain variable domain (VH). Together, the VH and VL domains form the antibody variable region (Fv) which is primarily responsible for antigen recognition/binding. The carboxy-terminal portions of the heavy and light chains together form a constant region primarily responsible for effector function.

As used herein, unless otherwise specified, an antibody referred to as comprising "a" specific light chain or "a" specific heavy chain in the singular refers to an antibody in which both light chains or both heavy chains are identical, respectively.

In some embodiments, the antibody being produced is cetuximab, palivizumab, rituximab, trastuzumab or a fragment thereof.

Also provided herein is a mammalian cell useful for increased production of a protein of interest comprising one or more of the nucleic acids constructs described herein. In some embodiments, the cell comprises two nucleic acid constructs described herein, each encoding a different protein of interest. In some embodiments, the protein of interest is an antibody or an antibody fragment as described herein, optionally cetuximab or a fragment thereof.

In one embodiment, the nucleic acid construct or constructs are stably transfected into the mammalian cell. In another embodiment, the construct or constructs are integrated into the genome of the mammalian cell.

The mammalian cell can be any mammalian cell. Suitable cells are well known in the art and may include, without limitation, SP2/0, NS/0, HT-1080 cells, PER.C6, HKB-11, CAP and HuH-7 human cell lines, Chinese Hamster Ovary (CHO) cells, and human embryonic kidney 293 (HEK293) cells. In one embodiment, the cell is a CHO cell, optionally a $CHO^{55E1}$ cell. In another embodiment, the mammalian cell is a Human Embryonic Kidney 293 (HEK293) cell.

Epstein-Barr nuclear antigen 1 (EBNA1) is integral to many EBV functions including gene regulation, extrachromosomal replication, and maintenance of the EBV episomal genome through positive and negative regulation of viral promoters. EBNA1 binds to sequence-specific sites at the EBV origin of viral replication (oriP) within the viral episome. EBNA1's specific binding ability, as well as its ability to tether EBV DNA to chromosomal DNA, allows EBNA1 to mediate replication and partitioning of the episomes during division of the host cell. The present inventors found that increased production of proteins from the mammalian cell in the presence of oriP occurred regardless of whether the EBNA1 gene was present. Accordingly, in an embodiment, the cell does not express EBNA1.

III. METHODS

The nucleic acids described herein may be used for the increased production of the protein of interest encoded therein. Accordingly, one aspect of the present disclosure is a method of increased production of a protein of interest, the method comprising: a) introducing into a cell a nucleic acid construct of the disclosure; b) applying selective pressure to the cell to select for cells that carry the selectable marker; and c) culturing the cell under conditions for production of the protein of interest.

Increased production as used herein refers to an increase of at least 5%, at least 10%, at least 20%, at least 30%, at least 40%, at least 50%, at least 60%, at least 70%, at least 80%, at least 90%, at least 100%, at least 150%, at least 200%, or at least 250% of protein production compared to proteins expressed from a nucleic acid construct lacking an oriP under the same conditions.

The nucleic acid construct may be introduced into the cell by any suitable method known in the art. In some embodiments, the nucleic acid construct is introduced into the cell by transfection, including calcium phosphate transfection and electroporation/nucleofection. Suitable transfection reagents are well known in the art and may include, without limitation, cationic polymers such as polyethylenimine (PEI), cationic lipids such as lipofectamine and related reagents (Invitrogen) and non-liposomal reagents such as Fugene and related reagents (Promega). In some embodiments, the nucleic acid construct is introduced into the cell by transfection using PEI.

Various cells may be used in the methods for production of the protein of interest. Suitable cells are well known in the art and may include, without limitation, SP2/0, NS/0, HT-1080 cells, PER.C6, HKB-11, CAP and HuH-7 human cells, Chinese Hamster Ovary (CHO) cells, and human embryonic kidney 293 (HEK293) cells. In some embodiments, the cell is a CHO cell, optionally a $CHO^{55E1}$ cell.

Epstein-Barr nuclear antigen 1 (EBNA1) is integral to many EBV functions including gene regulation, extrachromosomal replication, and maintenance of the EBV episomal genome through positive and negative regulation of viral promoters. EBNA1 binds to sequence-specific sites at the EBV origin of viral replication (oriP) within the viral episome. EBNA1's specific binding ability, as well as its ability to tether EBV DNA to chromosomal DNA, allows EBNA1 to mediate replication and partitioning of the episomes during division of the host cell. EBNA1 has been shown to only be able to replicate extrachromosomal DNA, and not chromosome-integrated DNA. EBNA1 has been shown to activate transcription (transactivate) from transfected templates. As demonstrated herein, expression of the EBNA1 protein is not required for enhanced protein production in the presence of the oriP sequences of the present disclosure. Accordingly, in some embodiments, the method is carried out in a cell that does not express EBNA1 protein.

The selective pressure applied to the cell will depend on the selective marker present in the nucleic acid construct. As used herein, the term "selective pressure" refers to the growth conditions of the cell that provide a selective advantage in cell viability for a cell harboring the selectable marker. Selective growth conditions may include, without limitation, the addition of a drug or the withdrawal of a component essential for growth. For example, where the selectable marker is an antibiotic resistance gene, selective pressure is applied by the addition of the antibiotic. As another example, where the selectable marker is glutamine synthetase, selective pressure is applied by the withdrawal of glutamine from the growth medium. In another example, the selective agent is methionine sulfoximine (MSX) for selection of glutamine synthetase overexpressing cells. In yet another embodiment, the selective marker is methotrexate for selection of dihydrofolate reductase (DHFR) expressing cells.

As described herein, the expression cassette of the nucleic acid construct may comprise an inducible promoter. Accordingly, in some embodiments, the conditions for the production of the protein of interest comprise the addition of an inducing agent. For example, where the inducible promoter is a cumate-inducible promoter, the conditions for the production of the protein of interest comprise the addition of comate to the growth medium.

As demonstrated herein, the protein being produced may be an antibody. The antibody heavy chain and antibody light chain may be encoded on separate nucleic acid constructs or may be encoded by two expression cassettes on the same nucleic acid construct. In some embodiments, the antibody is cetuximab.

In some embodiments, the method further comprises collecting the cell and/or a cell medium containing the protein of interest, and optionally purifying the protein of interest from the collected cell and/or the cell medium. Purification methods are known in the art and will depend on the protein being purified.

The following non-limiting examples are illustrative of the present disclosure:

IV. EXAMPLES

Example 1. Increased Stable Protein Production from Cells by Use of Epstein Barr Virus oriP Sequence In order to produce stable pools or stable cell lines expressing, for example, a single chain protein or antibodies, the gene of interest was cloned into one of our four different expression plasmids (Table 1).

TABLE 1

| Plasmid name | Features | Shown in FIG. |
|---|---|---|
| pTT75 ™ | Single CR5 promoter plasmid | 1C |
| pTT81 ™ | Single CR5 promoter plasmid + oriP | 1D |
| pTT96 ™ | Dual CR5 promoter plasmid | 1B |
| pTT109 ™ | Dual CR5 promoter plasmid + oriP | 1A |

In the context of a single chain protein, the gene was cloned either in pTT75™ or pTT81™.

In the context of an antibody, two approaches were used:

a) The heavy chain and light chain genes were cloned on separate pTT75™ or pTT81™ plasmids, and co-transfected into cells.

b) The heavy chain and light chain genes were cloned in a single vector each controlled by a CR5 promoter, either in pTT96™ or pTT109™ plasmids. Use of a single plasmid was sufficient for transfection in this case.

These plasmids contain the CR5 cumate-inducible promoter (proprietary of the National Research Council of Canada) combined with the rabbit beta-globin polyadenylation signal (pA) (GenBank accession number K03256) [1]. All derived from the pTT™ expression vector [2], these plasmids were engineered with a Glutamine Synthetase gene (GenBank accession number AY486122.1) which originated from HEK293-6E cells (Human Embryonic Kidney 293 cells clone 6E expressing EBNA1) as an amplifiable mammalian selectable marker under the control of the constitutive SV40 promoter (GenBank accession number J02400.1), combined with the strong bovine growth hormone polyadenylation signal (BGHpA) (GenBank accession number M57764.1) [3]. cDNA encoding the Glutamine Synthetase gene (GS) was synthesized by reverse-transcription/amplification using the ThermoScript™ RT-PCR System & Platinum® Taq DNA Polymerase kit (Invitrogen, USA) and mRNA isolated from HEK293-6E cells using the Micro FastTrack™ mRNA Isolation Kit (Invitrogen, USA). A Scaffold Attachment Region (SAR) which confers enhanced and persistent transgene expression was inserted upstream of the SV40 promoter [4]. The SAR sequence, which was synthesized by GeneArt™ Gene Synthesis Service, contains 750 nucleotides from the Human interferon alpha2 upstream scaffold associated region 3, nucleic acid sequence positions 1000 to 1751 (GenBank accession number U82705.1). The pMB1 ori and Ampicillin sequences are derived from the pcDNA3.1 vector (Thermo Fisher Scientific, USA).

EBNA1 is integral to many EBV functions including gene regulation, extrachromosomal replication, and maintenance of the EBV episomal genome through positive and negative regulation of viral promoters. Studies show that the phosphorylation of ten specific sites on EBNA1 regulates these functions. When phosphorylation does not occur, replication and transcription activities of the protein are significantly decreased. EBNA1 binds to sequence-specific sites at the origin of viral replication (oriP) within the viral episome. The oriP has twenty-four EBNA1 binding sites, including four in the Dyad Symmetry region (called DS) where replication is initiated as well as 20 sites in the Family of Repeats segment (called the FR). EBNA1's specific binding ability, as well as its ability to tether EBV DNA to chromosomal DNA, allows EBNA1 to mediate replication and partitioning of the episomes during division of the host cell. EBNA1 also interacts with some viral promoters via several mechanisms, further contributing to transcriptional regulation of EBNA1 itself as well as the other EBNAs (2 and 3) and of EBV latent membrane protein 1 (LMP1). EBNA1 has been shown to only be able to replicate extrachromosomal DNA, and not chromosome-integrated DNA.

The transient CHO-3E7 protein production system relies on CHO cells that express a codon-optimized and truncated version of EBNA1 protein [5]. Epstein-Barr nuclear antigen 1 (EBNA1) has been shown to activate transcription (transactivate) from transfected templates, but its ability to activate transcription from chromosome-integrated templates has been controversial [6]. To investigate if EBNA1 could transactivate regions of integrated oriP-containing plasmid DNA in CHO cells, stable $CHO^{55E1}$ cell lines stably expressing EBNA1, along with stable expression of cetuximab from plasmids containing or not containing the EBV oriP, were generated. The oriP, including two functional components, the dyad symmetry (DS) element and the family of repeats (FRs) derived from the Epstein-Barr virus (EBV) (GenBank accession number V01555.2) [7], was introduced downstream of the antibody expression cassette (CR5 promoter) and before the ampicillin resistance gene. The map of the pTT109™ plasmid is shown in FIG. 1A. Methods for cell culture, transfection, selection, induction of protein expression and purification were essentially as described in [3] and [8].

Figure 2:
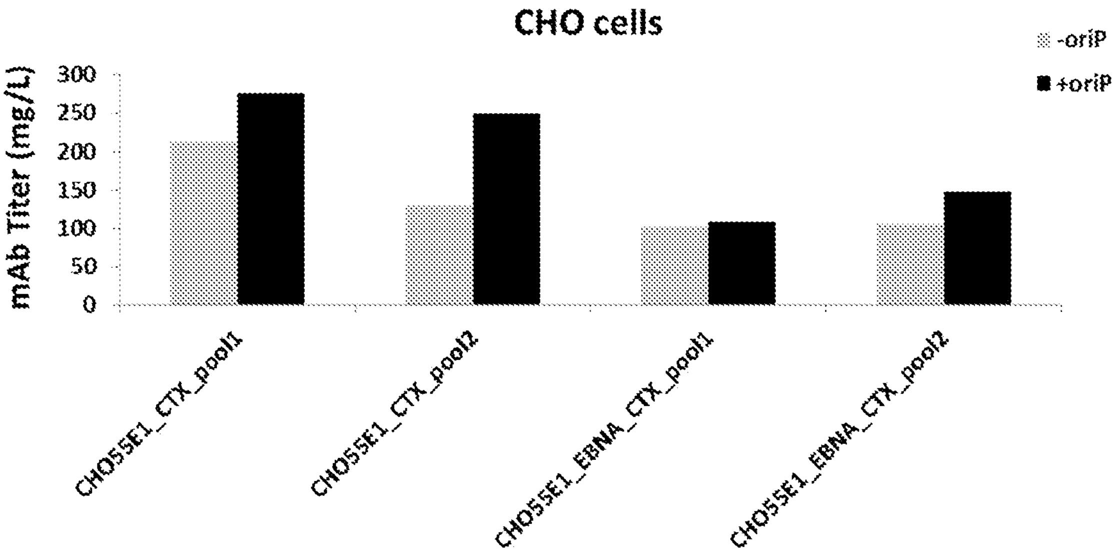
FIG. 2 shows stable pools generated with plasmid containing oriP have increased mAb productivity in EBNA1-negative CHO cells.

In contrast to the situation observed in CHO-3E7 cells, the presence of EBNA1 in the $CHO^{55E1}$ cells did not significantly increase cetuximab production when using oriP-containing plasmid (compared to non-oriP plasmid), suggesting that EBNA1 does not efficiently transactivate integrated oriP-containing plasmid DNA in $CHO^{55E1}$ cells. Further, the two pools generated with oriP-containing plasmid had significantly increased cetuximab productivity compared to non-oriP plasmid generated pools in non-EBNA1 $CHO^{55E1}$ cells (FIG. 2).

Figure 3:
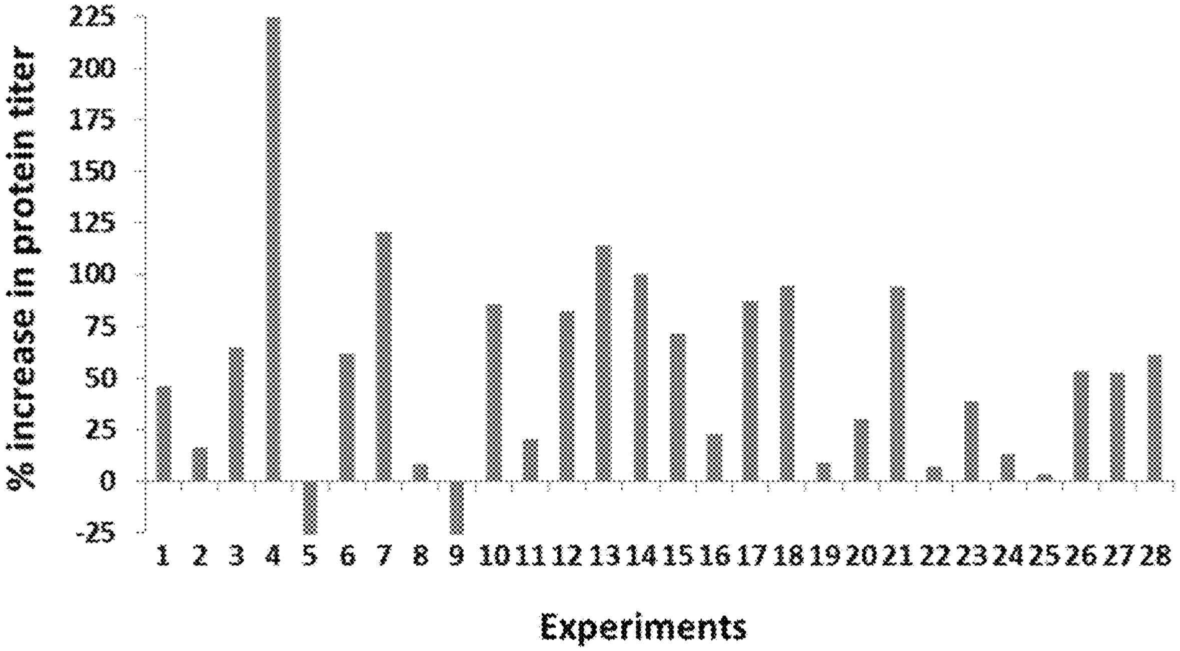
FIG. 3 shows the percent increase in protein titer in 28 stable pools generated with plasmid containing oriP compared to pool generating with plasmid without oriP.
Figure 4:
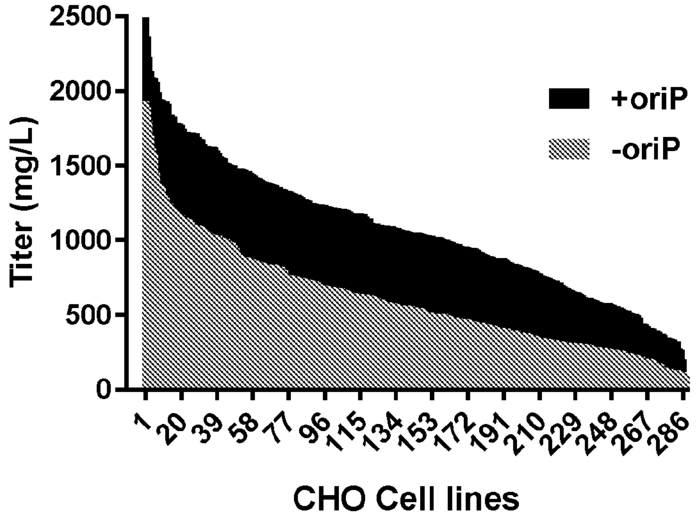
FIG. 4 shows protein production from 288 clones selected from pools generated with plasmid containing or not the EBV oriP.

Investigating this further, it was found that integration of the oriP sequence from Epstein Barr virus after the region encoding the gene of interest in the CR5-based expression plasmids almost always yielded stable cell pools with increased productivity. Ninety three percent (26 out of 28) of the pools that were generated with plasmid containing oriP had equal or increased productivity compared to control pools generated with plasmid not containing oriP (see FIG. 3). Throughout 28 experiments, productivity was increased by an average of 55% with a standard deviation of 52 (53% median). Improvement from the presence of oriP was similar when using either a single promoter approach (pTT81™ versus pTT75™) or a dual promoter approach (pill 09™ versus pTT96™). In addition, when single cell cloning was performed on two pools expressing an antibody, one generated through transfection of an oriP-containing plasmid (group 1), and the other generated through transfection of a plasmid without the oriP (group 2), the clones from the oriP pool (group 1) had increased productivity (FIG. 4). 288 group 1 clones had an average productivity of 1067 mg/L, compared to 608 mg/L for 288 group 2 clones (a 76% increase). Since, in a typical cloning project, only the top 96 producers are kept for the next round, the top 96 producers for group 1 had an average productivity of 1566 mg/L, versus 1006 mg/L for group 2 (a 56% increase).

Figure 1E:
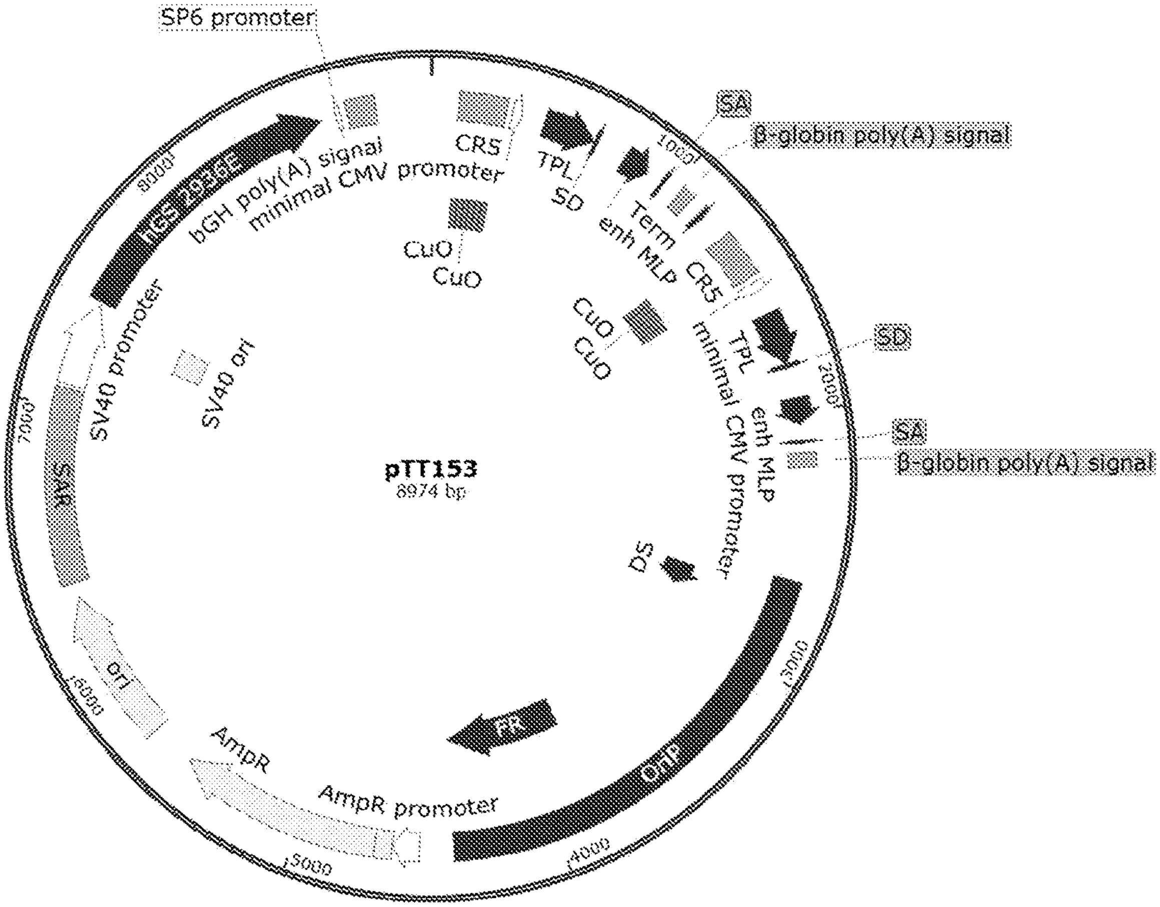
FIG. 1E shows pTT153™ plasmid map.
Figure 5:
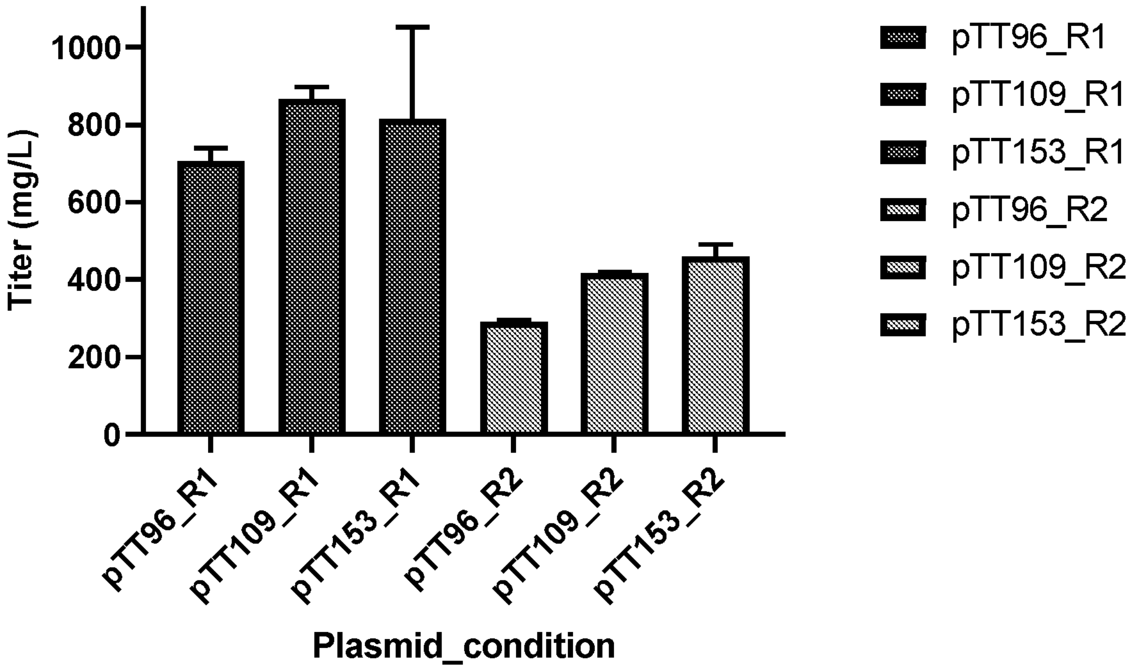
FIG. 5 shows stable CHO pool productivity from plasmids containing short (pTT109) or long (pTT153) oriP sequences.

To evaluate if this effect was also found with the original full length oriP sequence from EBV, another plasmid containing the full length oriP sequence (pTT153, shown in FIG. 1E) was generated and stable pool productivity for an antibody using two different feed regimens (R1 and R2) was compared. For R1, a commercial cell culture feed was added at 0, 3, 5, 7, 10, 12, 14 days post-induction, respectively at 1.5, 5, 5, 7.5, 5, 5, and 7.5% of the culture volume. For R2, another commercial cell culture feed was added at 0, 3, 5, 7, 10, 12, 14 days post-induction, respectively at 5, 5, 10, 15, 10, 10, and 7.5% of the culture volume. The plasmid pTT153 containing the full-length sequence or oriP increased stable pool productivity compared to pTT96 which did not contain the oriP sequence (FIG. 5). The increase in productivity with pTT153 was found to be similar to that obtained with a short oriP sequence (pTT109, shown in FIG. 1A).

Overall, the data suggest that for antibodies, using two plasmids containing oriP, such as the pTT81™ and pTT1109™ plasmids, confers increased pool productivity, which translates into increased likelihood of selecting clones with improved productivity. This increased productivity is also observed when using the full length sequence of EBV's oriP.

TABLE 2

| Sequences |
|---|
| Mini oriP (SEQ ID NO: 1)<br>ACCCTAAACGGGTAGCATATGCTTCCCGGGTAGTAGTATATACTATCCAG<br>ACTAACCCTAATTCAATAGCATATGTTACCCAACGGGAAGCATATGCTAT<br>CGAATTAGGGTTAGTAAAAGGGTCCTAAGGAACAGCGATGTAGGTGGGCG<br>GGCCAAGATAGGGGCGCGATTGCTGCGATCTGGAGGACAAATTACACACA<br>CTTGCGCCTGAGCGCCAAGCACAGGGTTGTTGGTCCTCATATTCACGAGG<br>TCGCTGAGAGCACGGTGGGCTAATGTTGCCATGGGTAGCATATACTACCC<br>AAATATCTGGATAGCATATGCTATCCTAATCTATATCTGGGTAGCATAGG<br>CTATCCTAATCTATATCTGGGTAGCATATGCTATCCTAATCTATATCTGG<br>GTAGTATATGCTATCCTAATTTATATCTGGGTAGCATAGGCTATCCTAAT<br>CTATATCTGGGTAGCATATGCTATCCTAATCTATATCTGGGTAGTATATG<br>CTATCCTAATCTGTATCCGGGTAGCATATGCTATCCTAATAGAGATTAGG<br>GTAGTATATGCTATCCTAATTTATATCTGGGTAGCATATACTACCCAAAT<br>ATCTGGATAGCATATGCTATCCTAATCTATATCTGGGTAGCATATGCTAT<br>CCTAATCTATATCTGGGTAGCATAGGCTATCCTAATCT |
| oriP (SEQ ID NO: 2)<br>GTAGCTACCGATAAGCGGACCCTCAAGAGGGCATTAGCAATAGTGTTTAT<br>AAGGCCCCCTTGTTAACCCTAAACGGGTAGCATATGCTTCCCGGGTAGTA<br>GTATATACTATCCAGACTAACCCTAATTCAATAGCATATGTTACCCAACG<br>GGAAGCATATGCTATCGAATTAGGGTTAGTAAAAGGGTCCTAAGGAACAG<br>CGATATCTCCCACCCCATGAGCTGTCACGGTTTTATTTACATGGGGTCAG<br>GATTCCACGAGGGTAGTGAACCATTTTAGTCACAAGGGCAGTGGCTGAAG<br>ATCAAGGAGCGGGCAGTGAACTCTCCTGAATCTTCGCCTGCTTCTTCATT<br>CTCCTTCGTTTAGCTAATAGAATAACTGCTGAGTTGTGAACAGTAAGGTG<br>TATGTGAGGTGCTCGAAAACAAGGTTTCAGGTGACGCCCCCAGAATAAAA<br>TTTGGACGGGGGGTTCAGTGGTGGCATTGTGCTATGACACCAATATAACC<br>CTCACAAACCCCTTGGGCAATAAATACTAGTGTAGGAATGAAACATTCTG<br>AATATCTTTAACAATAGAAATCCATGGGGTGGGGACAAGCCGTAAAGACT<br>GGATGTCCATCTCACACGAATTTATGGCTATGGGCAACACATAATCCTAG<br>TGCAATATGATACTGGGGTTATTAAGATGTGTCCCAGGCAGGGACCAAGA<br>CAGGTGAACCATGTTGTTACACTCTATTTGTAACAAGGGGAAAGAGAGTG<br>GACGCCGACAGCAGCGGACTCCACTGGTTGTCTCTAACACCCCCGAAAAT<br>TAAACGGGGCTCCACGCCAATGGGGCCCATAAACAAAGACAAGTGGCCAC<br>TCTTTTTTTTGAAATTGTGGAGTGGGGGCACGCGTCAGCCCCCACACGCC<br>GCCCTGCGGTTTTGGACTGTAAAATAAGGGTGTAATAACTTGGCTGATTG<br>TAACCCCGCTAACCACTGCGGTCAAACCACTTGCCCACAAAACCACTAAT<br>GGCACCCCGGGGAATACCTGCATAAGTAGGTGGGCGGGCCAAGATAGGGG<br>CGCGATTGCTGCGATCTGGAGGACAAATTACACACACTTGCGCCTGAGCG<br>CCAAGCACAGGGTTGTTGGTCCTCATATTCACGAGGTCGCTGAGAGCACG<br>GTGGGCTAATGTTGCCATGGGTAGCATATACTACCCAAATATCTGGATAG<br>CATATGCTATCCTAATCTATATCTGGGTAGCATAGGCTATCCTAATCTAT<br>ATCTGGGTAGCATATGCTATCCTAATCTATATCTGGGTAGTATATGCTAT<br>CCTAATTTATATCTGGGTAGCATAGGCTATCCTAATCTATATCTGGGTAG<br>CATATGCTATCCTAATCTATATCTGGGTAGTATATGCTATCCTAATCTGT<br>ATCCGGGTAGCATATGCTATCCTAATAGAGATTAGGGTAGTATATGCTAT<br>CCTAATTTATATCTGGGTAGCATATACTACCCAAATATCTGGATAGCATA<br>TGCTATCCTAATCTATATCTGGGTAGCATATGCTATCCTAATCTATATCT<br>GGGTAGCATAGGCTATCCTAATCTATATCTGGGTAGCATATGCTATCCTA<br>ATCTATATCTGGGTAGTATATGCTATCCTAATTTATATCTGGGTAGCATA<br>GGCTATCCTAATCTATATCTGGGTAGCATATGCTATCCTAATCTATATCT<br>GGGTAGTATATGCTATCCTAATCTGTATCCGGGTAGCATATGCTATCCTC<br>ACG |

REFERENCES

1. Mullick, A., et al., *The cumate gene-switch: a system for regulated expression in mammalian cells*. BMC. Biotechnol., 2006. 6: p. 43.
2. Durocher, Y., S. Perret, and A. Kamen, *High-level and high-throughput recombinant protein production by transient transfection of suspension-growing human* 293-*EBNA*1 *cells*. 2002. 30(2): p. 1-9.
3. Poulain, A., et al., *Rapid protein production from stable CHO cell pools using plasmid vector and the cumate gene-switch*. J Biotechnol, 2017. 255: p. 16-27.
4. Durocher, Y., U.S. Pat. No. 9,085,627—Expression system with SAR element from IFNa2. 2015, National Research Council of Canada 5. Durocher, Y. and M. Loignon, U.S. Pat. No. 8,637,315—Process, vectors and engineered cell lines for enhanced large-scale transfection. 2014, National Research Council Canada.
6. Kennedy, G. and B. Sugden, *EBNA-1, a bifunctional transcriptional activator*. Mol. Cell Biol., 2003. 23(19): p. 6901-6908.
7. Nanbo, A., A. Sugden, and B. Sugden, *The coupling of synthesis and partitioning of EBV's plasmid replicon is revealed in live cells*. EMBO J., 2007. 26(19): p. 4252-4262.
8. Poulain, A., et al., *Reducing recombinant protein expression during cho pool selection enhances frequency of high-producing cells*. J Biotechnol (2019) 296: p. 32-41.

What is claimed is:

1. A method of production of a protein of interest in a mammalian cell, the method comprising:

a) introducing into the mammalian cell a nucleic acid construct comprising a selectable marker;

b) applying selective pressure to the cell to select for cells that carry the selectable marker; and c) culturing the cell under conditions for production of the protein of interest, wherein the mammalian cell does not express Epstein-Barr virus nuclear antigen 1 (EBNA1) and wherein the nucleic acid construct comprises:

i) at least one expression cassette comprising a DNA sequence encoding the protein of interest operably linked to a promoter and a transcription termination site; and ii) an Epstein Barr virus (EBV) oriP or a fragment thereof comprising the dyad symmetry (DS) region and the family of repeats (FR) segment, wherein the mammalian cell is a Chinese hamster ovary (CHO) cell, wherein the oriP or fragment thereof comprises the nucleotide sequence set forth in SEQ ID NO: 1 or SEQ ID NO: 2, and wherein the protein of interest is an antibody or an antibody fragment.

2. The method of claim 1, wherein two different nucleic acid constructs are introduced into the cell and wherein each nucleic acid construct is as defined in claim 1.

3. The method of claim 1, wherein the nucleic acid construct comprises a Scaffold Attachment Region (SAR).

4. The method of claim 1, wherein the protein production is increased by at least 20% relative to protein production in a cell from a control nucleic acid construct lacking the oriP or fragment thereof when cultured under the same conditions.

5. The method of claim 1, wherein the nucleic acid construct is integrated into the genome of the mammalian cell.

6. The method of claim 1, wherein the method further comprises purifying the protein of interest.

7. The method of claim 1, wherein the nucleic acid construct encodes an antibody heavy chain and/or an antibody light chain, and the protein being produced is an antibody.

8. A mammalian cell for production of a protein of interest, the cell comprising a nucleic acid construct, wherein the cell does not express Epstein-Barr virus nuclear antigen 1 (EBNA1) and wherein the nucleic acid construct comprises:

a) at least one expression cassette comprising a DNA sequence encoding the protein of interest operably linked to a promoter and a transcription termination site;

b) a selectable marker; and c) an Epstein Barr virus (EBV) oriP or a fragment thereof comprising the dyad symmetry (DS) region and the family of repeats (FR) segment, wherein the mammalian cell is a Chinese hamster ovary (CHO) cell, wherein the oriP fragment comprises the nucleotide sequence set forth in SEQ ID NO: 1 or SEQ ID NO: 2, and where in the protein of interest is an antibody or antibody fragment.

9. The mammalian cell of claim 8, wherein the antibody or antibody fragment comprises a light chain variable domain (VL) and a heavy chain variable domain (VH) and the cell comprises two nucleic acid constructs, wherein one of the nucleic acid constructs encodes the VL and the other nucleic acid construct encodes the VH.

10. The mammalian cell of claim 8, wherein the nucleic acid construct is integrated into the genome.

11. The mammalian cell of claim 8, wherein the nucleic acid construct encodes an antibody heavy chain and/or an antibody light chain, and the protein being produced is an antibody.

12. The mammalian cell of claim 8, wherein the nucleic acid construct comprises a Scaffold Attachment Region (SAR).

* * * * *

SEQUENCE LISTING

<160> NUMBER OF SEQ ID NOS: 2

<210> SEQ ID NO 1
<211> LENGTH: 688
<212> TYPE: DNA
<213> ORGANISM: Epstein-Barr Virus

<400> SEQUENCE: 1
accctaaacg ggtagcatat gcttcccggg tagtagtata tactatccag actaacccta 60
attcaatagc atatgttacc caacgggaag catatgctat cgaattaggg ttagtaaaag 120
ggtcctaagg aacagcgatg taggtgggcg ggccaagata ggggcgcgat tgctgcgatc 180
tggaggacaa attacacaca cttgcgcctg agcgccaagc acagggttgt tggtcctcat 240
attcacgagg tcgctgagag cacggtgggc taatgttgcc atgggtagca tatactaccc 300
aaatatctgg atagcatatg ctatcctaat ctatatctgg gtagcatagg ctatcctaat 360
ctatatctgg gtagcatatg ctatcctaat ctatatctgg gtagtatatg ctatcctaat 420
ttatatctgg gtagcatagg ctatcctaat ctatatctgg gtagcatatg ctatcctaat 480
ctatatctgg gtagtatatg ctatcctaat ctgtatccgg gtagcatatg ctatcctaat 540
agagattagg gtagtatatg ctatcctaat ttatatctgg gtagcatata ctacccaaat 600
atctggatag catatgctat cctaatctat atctgggtag catatgctat cctaatctat 660
atctgggtag cataggctat cctaatct 688

<210> SEQ ID NO 2
<211> LENGTH: 1753
<212> TYPE: DNA
<213> ORGANISM: Epstein-Barr Virus

<400> SEQUENCE: 2
gtagctaccg ataagcggac cctcaagagg gcattagcaa tagtgtttat aaggccccct 60
tgttaaccct aaacgggtag catatgcttc ccgggtagta gtatatacta tccagactaa 120
ccctaattca atagcatatg ttacccaacg ggaagcatat gctatcgaat tagggttagt 180
aaaagggtcc taaggaacag cgatatctcc caccccatga gctgtcacgg ttttatttac 240
atggggtcag gattccacga gggtagtgaa ccattttagt cacaagggca gtggctgaag 300
atcaaggagc gggcagtgaa ctctcctgaa tcttcgcctg cttcttcatt ctccttcgtt 360
tagctaatag aataactgct gagttgtgaa cagtaaggtg tatgtgaggt gctcgaaaac 420
aaggtttcag gtgacgcccc cagaataaaa tttggacggg ggttcagtg gtggcattgt 480 gctatgacac caatataacc ctcacaaacc ccttgggcaa taaatactag tgtaggaatg 540
aaacattctg aatatcttta acaatagaaa tccatggggt ggggacaagc cgtaaagact 600
ggatgtccat ctcacacgaa tttatggcta tgggcaacac ataatcctag tgcaatatga 660
tactggggtt attaagatgt gtcccaggca gggaccaaga caggtgaacc atgttgttac 720
actctatttg taacaagggg aaagagagtg gacgccgaca gcagcggact ccactggttg 780
tctctaacac ccccgaaaat taaacggggc tccacgccaa tggggcccat aaacaaagac 840

-continued

```
aagtggccac tcttttttttt gaaattgtgg agtgggggca cgcgtcagcc cccacacgcc    900

gccctgcggt tttggactgt aaaataaggg tgtaataact tggctgattg taaccccgct    960

aaccactgcg gtcaaaccac ttgcccacaa aaccactaat ggcaccccgg ggaatacctg   1020

cataagtagg tgggcgggcc aagatagggg cgcgattgct gcgatctgga ggacaaatta   1080

cacacacttg cgcctgagcg ccaagcacag ggttgttggt cctcatattc acgaggtcgc   1140

tgagagcacg gtgggctaat gttgccatgg gtagcatata ctacccaaat atctggatag   1200

catatgctat cctaatctat atctgggtag cataggctat cctaatctat atctgggtag   1260

catatgctat cctaatctat atctgggtag tatatgctat cctaatttat atctgggtag   1320

cataggctat cctaatctat atctgggtag catatgctat cctaatctat atctgggtag   1380

tatatgctat cctaatctgt atccgggtag catatgctat cctaatagag attagggtag   1440

tatatgctat cctaatttat atctgggtag catatactac ccaaatatct ggatagcata   1500

tgctatccta atctatatct gggtagcata tgctatccta atctatatct gggtagcata   1560

ggctatccta atctatatct gggtagcata tgctatccta atctatatct gggtagtata   1620

tgctatccta atttatatct gggtagcata ggctatccta atctatatct gggtagcata   1680

tgctatccta atctatatct gggtagtata tgctatccta atctgtatcc gggtagcata   1740

tgctatcctc acg                                                      1753
```